US00PP33003P2

(12) United States Plant Patent
Knosher et al.

(10) Patent No.: US PP33,003 P2
(45) Date of Patent: Apr. 27, 2021

(54) ***GOMPHRENA* PLANT NAMED 'BALGOVARPUR'**

(50) Latin Name: *Gomphrena haageana*
Varietal Denomination: Balgovarpur

(71) Applicant: Ball Horticultural Company, West Chicago, IL (US)

(72) Inventors: Lynne Knosher, St. Charles, IL (US); Alan D. Blowers

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/007,914

(22) Filed: Aug. 31, 2020

(51) Int. Cl.
*A01H 6/02* (2018.01)
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Annette H Para
(74) *Attorney, Agent, or Firm* — Audrey Charles

(57) ABSTRACT

A new and distinct cultivar of *Gomphrena* plant named 'Balgovarpur', characterized by its red-purple colored inflorescences, medium yellow-green colored variegated foliage, and moderately vigorous, upright growth habit, is disclosed.

1 Drawing Sheet

Latin name of genus and species of plant claimed: *Gomphrena haageana.*

Variety denomination: 'Balgovarpur'.

BACKGROUND OF THE INVENTION

The present invention relates to a new and distinct cultivar of *Gomphrena* plant botanically known as *Gomphrena haageana* and hereinafter referred to by the cultivar name 'Balgovarpur'.

The new *Gomphrena* cultivar is a chemical-induced sport of QIS Carmine, not patented, characterized by its medium red-purple colored flowers, medium green-colored foliage, and moderately vigorous, upright growth habit. The mutagenic treatment occurred during September 2014. The new cultivar was discovered as a whole plant and selected during March 2015 in a controlled environment in Elburn, Ill.

Asexual reproduction of the new cultivar by terminal stem cuttings since March 2015 in West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balgovarpur' as a new and distinct cultivar of *Gomphrena* plant:

1. Red-purple colored inflorescences;
2. Medium yellow-green colored variegated foliage; and
3. Moderately vigorous, upright growth habit.

Plants of the new cultivar differ from plants of the parent primarily in having medium yellow-green colored variegated foliage.

Of the many commercially available *Gomphrena* cultivars, the most similar in comparison to the new cultivar is Truffula Pink 'PAST0517E', U.S. Plant Pat. No. 31,728.

However, in comparison, plants of the new cultivar differ from plants of 'PAST0517E' in at least the following characteristics:

1. Plants of the new cultivar have medium yellow-green colored variegated foliage that is different from the dark green-colored foliage of plants of 'PAST0517E;
2. Plants of the new cultivar have lighter green-colored stems than plants of 'PAST0517E; and
3. Plants of the new cultivar have fewer flowers per inflorescence than plants of 'PAST0517E'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balgovarpur'. The plants were approximately four months old. The plants were grown in 4-inch pots for approximately 12 weeks in a greenhouse in West Chicago, Ill. Plants were given one pinch at transplant.

DETAILED BOTANICAL DESCRIPTION

Figure 1:
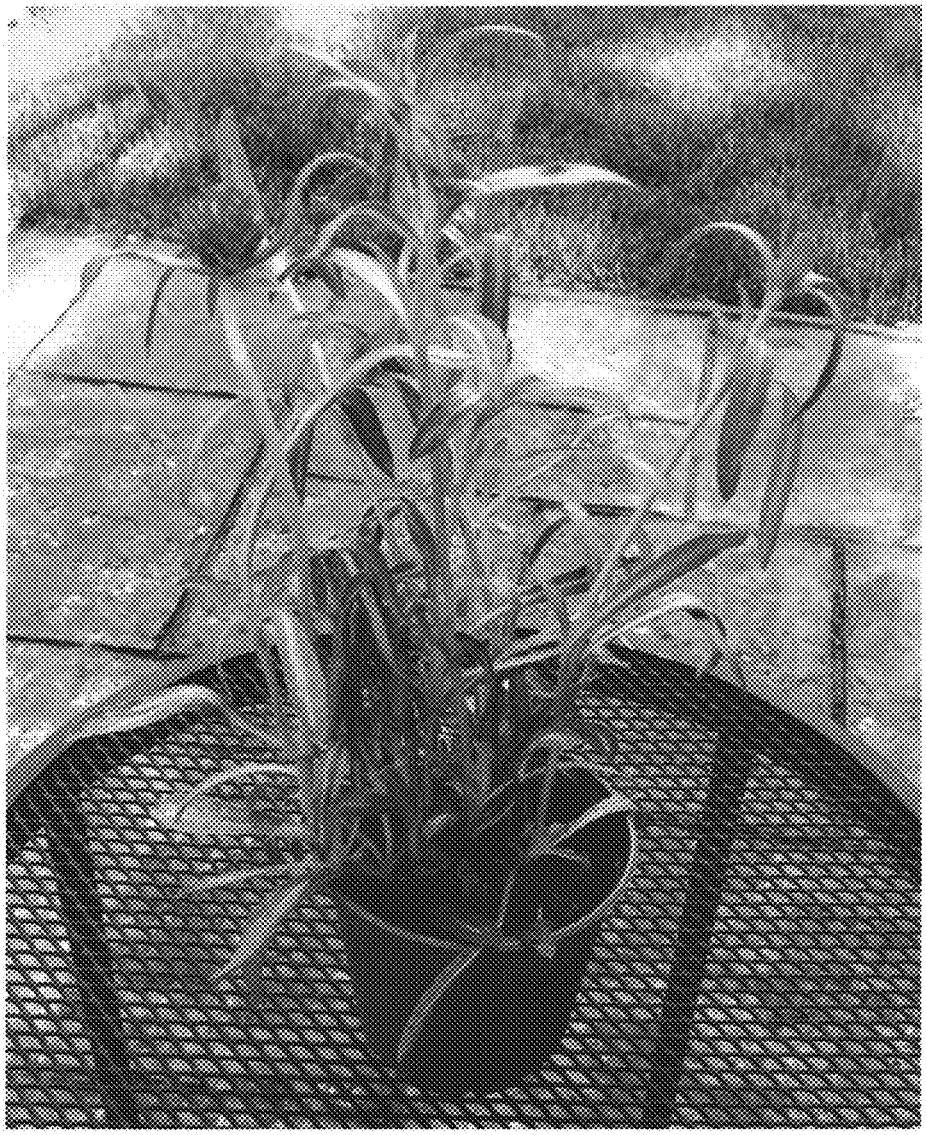
FIG. 1 illustrates a side view of the overall growth and flowering habit of 'Balgovarpur'.
Figure 2:
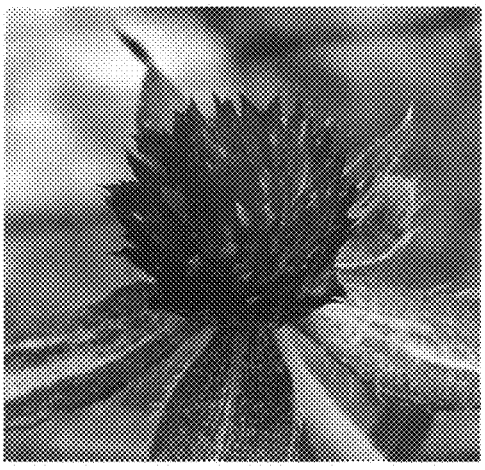
FIG. 2 illustrates a close-up view of an individual inflorescence of 'Balgovarpur'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2020 under natural light conditions in Naperville, Ill.

The following descriptions and measurements describe approximately 4-month old plants produced from cuttings from stock plants and grown in a poly-covered greenhouse under conditions comparable to those used in commercial practice. The plants were grown in West Chicago, Ill. in 4-inch pots for approximately 12 weeks utilizing a soilless growth medium. Plants were given one pinch at transplant. Temperatures ranged from an average high of 75.0° F. (23.9° C.) to an average low of 70.0° F. (21.1° C.), and supplemental lighting was provided daily for five hours during short days. Measurements and numerical values represent averages of typical plants.

Botanical classification: *Gomphrena haageana* 'Balgovarpur'.

Parentage:

*Parent.*—QIS Carmine, not patented.

Propagation:

*Type cutting.*—Terminal stem.

*Time to initiate roots.*—Approximately 12 to 14 days.

*Time to produce a rooted cutting.*—Approximately 5 to 6 weeks.

*Root description.*—Fibrous, fine.

*Rooting habit.*—Freely branching, moderate density.

Plant description:

*Commercial crop time.*—Approximately 6 to 8 weeks from a rooted cutting to finish in a 15 cm pot.

*Growth habit and general appearance.*—Annual, moderately vigorous, upright.

*Size.*—Height from soil level to top of plant plane: Approximately 33.0 cm. Width: Approximately 30.0 cm.

*Branching habit.*—Freely branching, pinching enhances basal branching. Quantity of lateral branches per plant: Approximately 9.

*Branch.*—Shape: Rounded, sometimes crooked. Strength: Strong. Length: Approximately 7.0 cm to 22.0 cm. Diameter: Approximately 3.0 mm to 4.0 mm. Length of central internode: Approximately 4.5 cm to 7.0 cm. Texture: Densely pubescent with long, appressed hairs. Color of young stem: 145B lightly tinted with 187C. Color of mature stem: 145A lightly tinted with 187C.

Foliage description:

*General description.*—Quantity of leaves per lateral branch: Approximately 6 to 8. Fragrance: None detected. Form: Simple. Arrangement: Opposite.

*Leaves.*—Aspect: Perpendicular to stem. Shape: Lanceolate, slightly keeled. Margin: Entire. Apex: Apiculate. Base: Sessile. Venation pattern: Pinnate. Length of mature leaf: Approximately 8.5 cm. Width of mature leaf: Approximately 1.5 cm. Texture of upper surface: Moderately pubescent. Texture of lower surface: Densely pubescent. Color of upper surface of young and mature foliage: 137A with a central variegation pattern of N144D, venation color indistinguishable from laminae. Color of lower surface of young and mature foliage: Closest to 147B with a central variegation pattern of closest to but lighter than 146D, venation color indistinguishable from laminae.

Flowering description:

*Flowering habit.*—'Balgovarpur' is freely flowering under outdoor growing conditions with substantially continuous blooming from spring through autumn.

*Lastingness of individual inflorescence on the plant.*—Approximately 30 days.

Inflorescence description:

*General description.*—Type: Clover-like, papery-like heads, persistent. Quantity per plant: Approximately 2. Fragrance: None detected. Aspect: Facing upward or outward. Height: Approximately 1.8 cm. Width: Approximately 1.7 cm. Quantity of fully open flowers per inflorescence: Approximately 40.

*Peduncle.*—Strength: Strong, slightly flexible. Shape: Round. Aspect: Erect to acute angle to stem, often crooked. Length: Approximately 9.0 cm to 12.0 cm. Diameter: Approximately 3.0 mm. Texture: Densely pubescent with long, appressed hairs. Color: 145B often lightly tinted with 187C.

Flower description:

*General description.*—Type: Tubular, sessile with a five-parted perianth in a single whorl subtended by two bracts.

*Bud just before opening.*—Shape: Ovoid. Length: Approximately 7.0 mm. Diameter: Approximately 2.0 mm. Color: NN155D with NN78A.

*Perianth segments.*—Quantity: 5. Shape: Lanceolate. Margin: Entire. Apex: Acute. Base: Truncate. Length: Approximately 8.0 mm. Width: Approximately 1.0 mm. Texture: Glabrous with sericeous base, translucent, papery-like. Color of inner surface: NN155D with N78C at tip. Color of outer surface: NN78A, transitioning with age to N78B and N78A, NN155D at base.

*Bracts.*—Quantity per flower: 2 per flower. Shape: Ovate, keeled. Length: Approximately 1.0 cm. Width: Approximately 4.0 mm. Texture of upper and lower surfaces: Glabrous, translucent, papery-like. Color of upper and lower surfaces: NN155D with tip of NN78A, tip transitions with age to N78B to N78A.

*Reproductive organs.*—Androecium: Stamen quantity and arrangement: Filaments united into a cylindrical tube with five acute tips, tube encases the gynoecium. Filament length: Approximately 9.0 mm. Filament tube width: Approximately 1.0 mm. Color of outer and inner surfaces of filament tube: NN155D with tips of 14B and base of 145D. Anther shape: Oblong, dorsifixed to filament tip. Anther length: Approximately 1.5 mm. Anther color: 14D. Pollen amount: Sparse. Pollen color: 14D. Gynoecium: Pistil quantity: 1 per flower. Pistil length: Approximately 3.0 mm. Stigma shape: Bi-parted. Stigma length: Approximately 1.5 mm. Stigma color: 145D, translucent. Style length: Less than 1.0 mm. Style color: 146D. Ovary diameter: Approximately 1.0 mm. Ovary color: 146D.

Seed and fruit production: Neither seed nor fruit production has been observed.

Disease and pest resistance: Resistance to pathogens and pests common to *Gomphrena* has not been observed.

What is claimed is:

1. A new and distinct cultivar of *Gomphrena* plant named 'Balgovarpur', substantially as herein illustrated and described.

* * * * *